United States Patent [19]

Mangold

[11] Patent Number: 5,306,622

[45] Date of Patent: Apr. 26, 1994

[54] HETEROGENEOUS IMMUNOASSAY PROCESS

[75] Inventor: Dieter Mangold, Mannheim, Fed. Rep. of Germany

[73] Assignee: Boehringer Mannheim GmbH, Mannheim, Fed. Rep. of Germany

[21] Appl. No.: 788,173

[22] Filed: Nov. 5, 1991

Related U.S. Application Data

[63] Continuation of Ser. No. 195,604, May 18, 1988, abandoned.

[30] Foreign Application Priority Data

May 29, 1987 [DE] Fed. Rep. of Germany ....... 3718140

[51] Int. Cl.$^5$ ........................................... G01N 33/543
[52] U.S. Cl. ..................................... 435/7.92; 435/7.9; 435/7.93; 435/7.94; 435/962; 435/967; 435/970; 435/973; 436/544; 436/546; 436/805; 436/810; 436/518
[58] Field of Search ............... 435/7.9, 4, 7.92–7.94, 435/810, 962, 967, 970, 973; 436/501, 514, 518, 544, 546, 810, 805

[56] References Cited

U.S. PATENT DOCUMENTS

| | | | |
|---|---|---|---|
| 4,387,164 | 6/1983 | Hevey et al. | 436/45 |
| 4,540,659 | 9/1985 | Litman et al. | 435/967 X |
| 4,803,170 | 2/1989 | Stanton et al. | 436/518 |

FOREIGN PATENT DOCUMENTS

| | | | |
|---|---|---|---|
| 0264866 | 4/1988 | European Pat. Off. | 435/962 |
| 8002076 | 10/1980 | PCT Int'l Appl. | |

OTHER PUBLICATIONS

ALDRICH Chemical Company 1986 Catalog p. 24.

Primary Examiner—Esther L. Kepplinger
Assistant Examiner—Carol A. Spiegel
Attorney, Agent, or Firm—Felfe & Lynch

[57] ABSTRACT

The invention teaches a method for determining an analyte in a liquid sample via a heterogeneous assay. The sample is contacted to a carrier material which contains, in addition to one of a labelled analyte analogous substance or a labelled analyte specific substance, a detectable component which does not influence immunological reactions occurring during the course of the assay. A solid phase bound component, which is either an insufficient amount of analyte specific substance or an excess of analyte relative to analyte in the sample is contacted to the sample so as to accomplish formation of solid phase bound complexes. After separation of liquid and solid phase, label is measured in one of these, and the detectable substance is measured in the liquid. Correlation of the values obtained leads to determination of the analyte. Also described is a reagent used in the described method.

6 Claims, 2 Drawing Sheets

FIG. 1
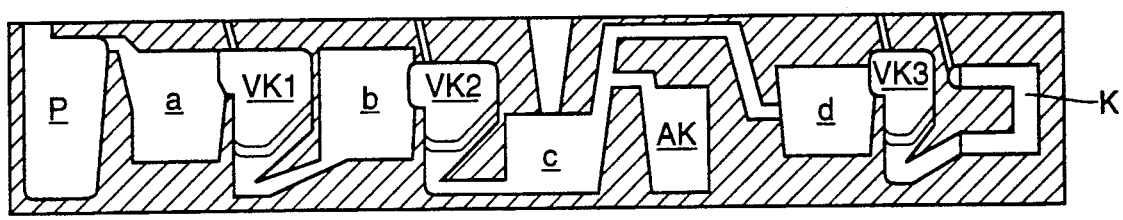
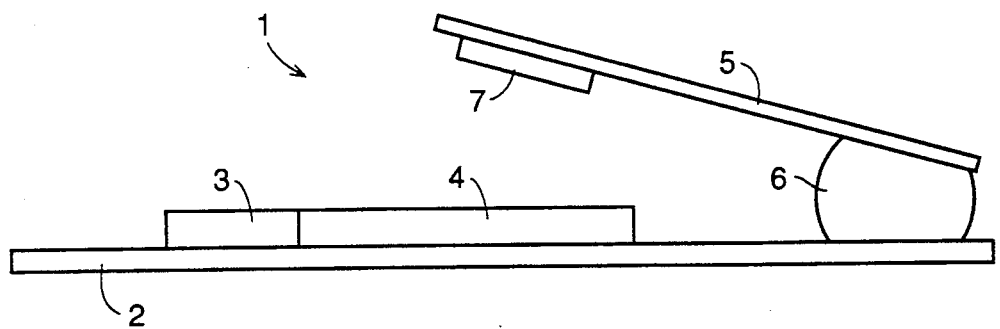
FIG. 4

HETEROGENEOUS IMMUNOASSAY PROCESS

This application is a continuation of application Ser. No. 07/195,604, filed May 18, 1988, now abandoned.

The present invention is concerned with a heterogeneous immunological process for the determination of an analyte in a solution in which at least one component of the immunological reaction is dissolved from a carrier material before and/or during the incubation.

Heterogeneous immunoassays include, for example, competitive assays. In general, such test processes involve competition between a known amount of labelled analyte and an unknown amount of an unlabelled analyte to be determined for a limited amount of an analyte-specific, solid phase-bound component of an immunological reaction. After carrying out the immunological reaction, the solid phase-bound, labelled analyte can be separated from the free, labelled analyte and the amount thereof determined chemically or physically by means of the label. The size of the measurement value determined is inversely proportional to the amount of the unlabelled analyte present in the sample. As an alternative, there can also be determined the amount of labelled analyte which remains unbound. In this case, the size of the measurement value is directly proportional to the amount of the analyte present in the sample.

An example of such a competitive heterogeneous immunoassay is the ELISA test (enzyme-linked immunosorbent assay) in which, as analyte in the sample, there is usually determined an antigen which competes with labelled antigens for a solid phase-bound antibody. As label, there is used an enzyme, for example $\beta$-D-galactosidase, peroxidase or an alkaline phosphatase. In principle, however, all possible labels, for example radio-active isotopes, fluorescent labels and the like, can be used in competitive immunoassays.

Another heterogeneous immunoassay in which an enzyme is used as label is the immunoenzymometric assay (IEMA). In contrast to the ELISA test, this type of assay uses, for example for the determination of antigens, labelled antibodies and solid phase-bound antigens. In the homogeneous phase, the reaction between antigen and an excess of labelled antibody first takes place. The excess of labelled antibody is then removed by solid phase-bound antigen and subsequently the amount of solid-bound label or of unbound label is determined. Here, too, the size of the measurement value obtained on the solid phase is inversely proportional to the amount of the unlabelled antigen to be determined in the sample. The size of the measurement value obtained for the unbound label is directly proportional to the amount of the antigen to be determined in the sample.

Very frequently, heterogeneous immunoassays are carried out in such a manner that the individual reaction components and the reagents are manually mixed together and subsequently incubated, the solid phase is manually separated from the liquid phase and, possibly after a washing step, the amount of the label is determined. In order to simplify such immunoassays, to increase the sensitivity and reproducability thereof and to save time and personnel, carrier-bound tests or means for automated tests have been developed.

Thus, for example, in U.S. Pat. No. 4,446,232 a device for the determination of antigens which consists of two zones is described. In the first zone, there is present enzyme-labelled antibodies and immobilized antigens. The second zone contains material which is able to react with the enzyme-labelled antibodies and to produce a color thereby. If an antigen-containing sample is applied to such a device, these react with the enzyme-labelled antibodies, excess antibodies being bound to the carrier via the immobilized antigens. Antibodies which have reacted with free antigen to be determined are transported with the liquid of the sample into the second zone and reaction of the enzyme label with the second zone material leads to the formation of a color, the intensity of which is proportional to the antigen concentration to be determined in the sample.

U.S. Pat. No. 4,690,899 is concerned with a process and device for the automated carrying out of analytical determinations such as immunological assays. For the determination of a hapten or antigen in a sample liquid, an antibody-enzyme conjugate, which is present in known amount on a reagent carrier, is eluted from this carrier and is incubated with the sample solution. A soluble complex is formed of hapten or antigen and conjugate, along with excess free conjugate. Under the influence of cycles of changing force, this mixture is then passed to a region in which further hapten or antigen is present in insoluble phase. Excess conjugate still present is there retained, whereas liquid containing the hapten conjugate complex or antigen conjugate complex is further transported to a dry reagent for the determination of the enzyme bound in the conjugate, dissolves or elutes this and, in a further force-changing cycle, is finally transported to a measurement cuvette in which a physical change brought about by the enzyme reagent is measured.

Carrier-bound tests and automated tests frequently utilize a known concentration and amount of labelled reaction component of the immunological reaction of the test in a carrier material. This labelled component must be eluted from the carrier, and the eluted amount of the labelled reaction component is known precisely. For the determination of the label as the last step of heterogeneous immunoassays, the measurement value is associated, by means of a calibration curve, with the analyte concentration which represents the value to be determined. In order to achieve reproducible results, the samples to be determined must be measured under the same conditions as the samples of known concentration used for the production of the calibration curve. It is important for the reproducability and precision of the carrier-bound or automated heterogeneous immunoassay to know the precise concentration of the labelled reaction component of the immunological reaction in the incubation solution. Problems can arise when different batches of carrier material, labelled immunological reaction components or carrier materials impregnated with these are used.

When carrier-bound and automated tests use enzyme-antibody conjugates impregnated on a carrier material, the eluted concentration of the labelled reaction component of an immunological reaction, for example of the enzyme-antibody conjugate in an IEMA test, is dependent not only upon the actual concentration of the reaction component on the carrier material but also upon the quality of the carrier material and of the quality of the conjugate. Reasons for the differing concentration adjustments of the labelled reaction component of an immunological reaction, as in the case of a test according to U.S. Pat. Nos. 4,446,232 and 4,690,899 can include the batch-dependent property of the conjugate of label and component of an immunological reaction;

differing absorption behavior and different elutability as a result of inhomogeneities of the carrier material; or differing amount of conjugate on an individual test zone due to non-homogeneous loading and measurement tolerances in the production of the individual test zones from the carrier material.

The differing concentrations of labelled reaction component of an immunological reaction in an eluate hereby brought about can lead to results with relatively large variation coefficients.

Therefore, there is a need for a heterogeneous, immunological process in which the result is not influenced by the possibly varying amount of the labelled reaction component of an immunological reaction eluted from the solid carrier material from one sample to another.

It is an object of the present invention to satisfy this need.

Thus, according to the present invention, there is provided a heterogeneous immunological process for the determination of an analyte in a sample in which at least one component of an immunological reaction is dissolved from a carrier material, the analyte-containing sample being incubated with a labelled, analyte-analogous or analyte-specific component of an immunological reaction dissolved from a carrier material, contacted with an insufficiency of the analyte-specific component of an immunological reaction or with an excess of the analyte to be determined in carrier-bound form, the bound and the free part of the immune complex thus formed being separated and the label measured in the free or bound part, wherein the carrier material additionally contains a detectable substance not influencing the immunological reaction which is eluted together with the component of the immunological reaction and a characteristic measurement value obtained for the concentration of the detectable substance in the solution is correlated with the measurement value of the analyte concentration in the sample.

"Analyte" as referred to herein includes every kind of hapten or antigen as well as antibody. By "labelled, analyte-analogous component of an immunological reaction" is to be understood a labelled hapten, antigen or antibody corresponding to the hapten, antigen or antibody to be determined, "corresponding" thereby meaning that the labelled substance behaves like the unlabelled substance to be determined in immunological reactions.

"A component of an immunological reaction" refers to a hapten or antigen and an antibody directed against this hapten or antigen and reacting therewith. Such reactive components of an immunological reaction react with one another very specifically with the formation of immune complexes (hapten-antibody or antigen-antibody complexes). The immunological component which can so react with the analyte to be determined is, therefore, designated as being "analyte-specific".

The detectable substances can be all those substances which, on the basis of their physical properties, such as radio-activity, fluorescence, color, color formability or the like, permit a measurement of their concentration and which, at the same time, display an elution behavior comparable to the conjugate of immunological reaction component and label to be eluted. Fluorescing compounds and colored materials have proved to be especially preferable.

The detectable control substance is to be chosen depending upon the nature of the conjugate of immunological reaction component and label. This must not influence the chemical and physical properties of the immunological reaction component, those of the label, the reaction of the conjugate or label, or the reaction of the immunological reaction component with a second immunological reaction component to be determined. The measurement of the label must also not be disturbed by the detectable substance. It is especially important that the detectable substance, which is present together with the conjugate of label and immunological reaction component impregnated in the carrier material, does not influence the stability of the label. Furthermore, it is also important that the homogeneity of the impregnation solution is not influenced by the control substance.

In particular, the choice of the detectable control substance depends upon the nature of the label of the immunological reaction component. If, for example, an enzyme is used as label of the immunological reaction component which is detected with the help of a chromogenic substrate, then, as detectable substance, there is especially preferred a colored material, the absorption range of which differs sufficiently clearly from the absorption range of the chromogenic substrate or of the substance which results therefrom by the enzymatic reaction. In such a case, a substrate can also be selected which can be detected with the help of a different physical measurement process, for example a fluorescing colored material or a radioactively labelled substance, which can be measured fluorometrically or radiometrically. Numerous further appropriate combinations of label and detectable substances can readily be ascertained on the basis of the above statements. For the special case in which $\beta$-galactosidase is employed as label, which can be detected by o-nitrophenylgalactoside or chlorophenol red galactoside, the group of compounds known as patent blues is especially preferred as detectable substances. The absorption of o-nitrophenol and chlorophenol red, which are liberated from the corresponding galactosides by galactosidase, lies in the range below 600 nm, whereas the patent blues show absorptions which lie above this range. Thus, these colored materials can be measured at 650 nm independently and without disturbance of the $\beta$-galactosidase measurement.

Patent blues are known colored materials of the following structure:

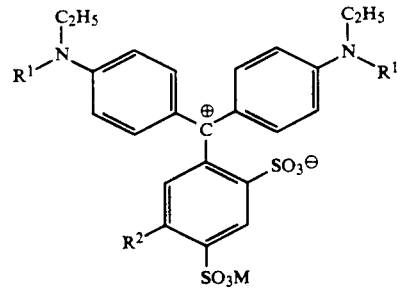

in which $R^1$ is a lower alkyl or aralkyl radical, $R^2$ is a hydrogen atom or a hydroxyl group and M is an alkali metal or an alkaline earth metal equivalent.

By a lower alkyl radical of the substituent $R^1$ is to be understood a straight-chained or branched, saturated or unsaturated hydrocarbon radical containing up to 6 and preferably up to 4 carbon atoms. The aralkyl radical of the substituent $R^1$ has a hydrocarbon chain containing up to 3 carbon atoms which is substituted with one or more aromatic radicals, the phenyl radical being preferred. The benzyl radical is especially preferred as aralkyl radical. Preferred alkali metal atoms are sodium and potassium and preferred alkaline earth metal atoms are magnesium and calcium. The colored materials disulphine blue ($R^1$=ethyl; $R^2$=hydrogen and M=sodium), as well as patent blue AF (acid blue 7; $R^1$=benzyl, $R^2$=hydrogen and M=sodium) are especially preferred.

As carrier materials, there can be used all conventional materials which are appropriate for impregnation with immunological substances. According to the present invention, cellulose, paper and also synthetic resin materials and mixtures thereof have proved to be especially useful.

For the preparation of a carrier material which is impregnated not only with a detectable substance but also with a conjugate, the detectable substance is preferably added to the conjugate impregnation solution, the carrier material being impregnated with this solution and subsequently dried. Consequently, the present invention also provides an agent for the immunological determination of an analyte in a sample, comprising a carrier material which is impregnated with a labelled, analyte-analogous or analyte-specific component of an immunological reaction, wherein it is additionally impregnated with a detectable substance.

If the carrier material so produced is used in a heterogeneous immunological test, then not only the labelled analyte-analogous or analyte-specific component of an immunological reaction is eluted from the carrier material but also the detectable substance. The detectable substance is subjected to the same concentration variations as the labelled component not only on the carrier material but also in the elution solution. The detectable substance does not participate in the immunological reaction. After incubation and separation of the bound and free part, on the one hand, the label is determined in the usual manner and, on the other hand, the dissolved amount of detectable substance is determined. From variations of the measurement signal for the detectable substance ascertained from sample to sample, there can be directly concluded the analogous concentration variations of the labelled component of the immunological reaction.

For this purpose, the intensity of the measurement signal for the detectable substance, for example of the patent blue signal, can be measured at 650 nm in several tests of one test batch, the average value obtained and the deviation of the particular measurement value from the average value calculated as a percentage. This percentage value can then be used for the correction of the measurement value of an analyte determination.

In the case of using β-galactosidase as enzyme label, there was found, for example, a linear relationship between the color intensity of the colored material eluted from the carrier material, for example disulphine blue or other patent blues and the eluted enzyme label. An alteration in the eluted enzyme label leads to a corresponding change of the measurement value for the detectable substrate, i.e. a variation in the conjugate dosaging passes through completely to the control signal, whereby, by this, in the special case of a colored material, the color intensity is to be understood as detectable substance.

If a sample with the analyte to be determined is incubated with an excess of an analyte-specific component of the immunological reaction which is labelled, for example with β-galactosidase and has been eluted together with a detectable substance, for example disulphine blue, from a carrier and if, subsequently, the excess component of the immunological reaction is taken up with analytes bound to a matrix and subsequently a characteristic measurement value for the label and for the detectable substance is determined, then, as measurement result, there is obtained:

1. a signal for the detectable substance: $X_F$
2. A signal for the label: $X_A$ From $X_A$, the concentration of the analyte $C_A$ can be determined from a calibration curve obtained in the usual way.

This analyte concentration can be corrected on basis of the signal for the detectable substance according to the following general equation:

$$C_{corrected} = C_A + f \cdot \left[ \frac{(\overline{X}_F - X_F)}{\overline{X}_F} \right] \cdot C_A$$

wherein:
$C_{corrected}$ = corrected analyte concentration (improved measurement result)
$C_A$ = analyte concentration (determined from the measurement value via a calibration curve)
$X_F$ = signal for the detectable substance of the determination in question
$\overline{X}_F$ = average value signal for the detectable substance for a test batch
f = an analyte-specific empirical factor.

The average $\overline{X}_F$ is obtained by determining the signals for the detectable substance from several tests of a particular test batch and calculating the average value herefrom. By a test batch is hereby to be understood all tests in the production which, for the impregnation of the carrier material, there has been used the same impregnation solution with the labelled partner of the immunological reaction and of the detectable substance.

The analyte-specific factor f is determined by measuring, in the above manner, several samples with known analyte concentrations, using the found measurement data in the above equation and, having regard to the batch-specific average $\overline{X}_F$, calculating the particular related factor f as average value. As concentration $C_{corrected}$ is hereby, in each case, to be used the previously known analyte concentration. We have found that, in this way, there is obtained a factor specific for a particular analyte. This is, for example, 0.5 for digoxin and 0.65 for T3.

With the help of the process according to the present invention, it is possible to control the stability of conjugate impregnation solutions by measurement after different times, to avoid balancing difficulties in the case of testing for drying losses and recovery rates, to test for batch homogeneities, to determine variations of label properties, for example of the enzymatic activity, which can be caused by raw material influences, by reference measurement and to test for the influence of concentration variations of the conjugate on the whole immunological test.

In the drawings,

FIG. 1 is a schematic diagram of an immunoassay reaction chamber of this invention.

FIG. 4 is a diagram of another embodiment of the device of the present invention.

Figure 2:
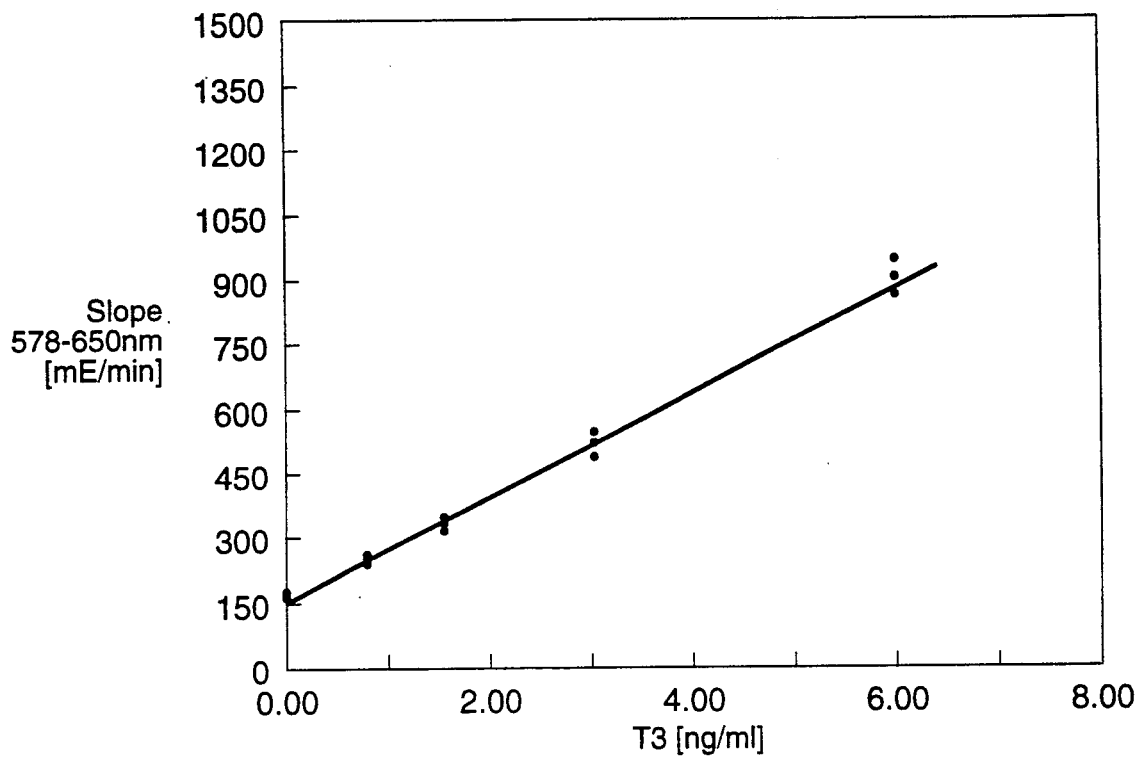
FIG. 2 is a T3 calibration curve obtained using this invention.

An example of a device with which the process according to the present invention can be carried out is shown in FIG. 4 of the accompanying drawings. The device 1 comprises a base film 2 on which is fixed a conjugate fleece 3 according to the present invention standardized with a detectable substance, a matrix 4 which contains an insufficient amount of the analyte-specific component of the immunological reaction or an excess of the analyte to be determined in carrier-bound form, as well as a film 5 which is fixed via a point of adhesion 6 to the base film 2. On the film 5 is applied a substrate film 7 on the side of the film facing the matrix 4.

For the determination of an analyte in a liquid, the sample is applied to the conjugate fleece 3. The liquid with the materials dissolved from the fleece 3 is transported by capillary forces into the matrix 4. For the measurement of the label, the film 5 with the substrate film 7 is pressed on to the matrix 4. After a fixed period of time, there is determined the measurement value of the detectable substance and the measurement value caused by the reaction of the label with the substrate. The analyte concentration is corrected as described hereinbefore.

The present invention is, of course, not limited to the device according to FIG. 4. Devices which can be used for heterogenic immunoassays can be readily modified in the manner according to the present invention.

The present invention is also concerned with the use of a substance detectable on the basis of its physical properties for the control of the concentration of a labelled component of an immunological reaction eluted from a carrier material. Such materials which can be detected on the basis of their physical properties are, in particular, fluorescing compounds and colored materials. For the control of the concentration of $\beta$-galactoside-labelled antibodies, there are especially preferred patent blues, such as disulphine blue.

The process according to the present invention for the determination of a component of an immunological reaction and the use herefor of appropriate detectable substances is explained in more detail in the following Examples:

EXAMPLE 1

Preparation of a conjugate fleece standardized with patent blue colored material Fleece material (80% polyester and 20% regenerated cellulose consolidated with KURALON ®; absorptive capacity about 600 ml./m²) is impregnated with a solution of the following composition and dried with circulating air.

Impregnation solution sodium HEPES buffer, 100 mM, pH 7.25
polyoxygelatin 1%
magnesium aspartate 5 mM
anti-T3 monoclonal antibody Fab fragment 280 U/l.
disulphine blue 0.0015%.

EXAMPLE 2

Determination of T3

A) Determination of T3 as an example of a hapten using an insert element according to FIG. 1 of the accompanying drawings (conjugate fleece without detectable substance). Loading of the insert element according to FIG. 1 chamber a) 2 fleece, each of 0.5 mm. thickness, impregnated with:
sodium HEPES, 125 mM, pH 7.25
TWEEN ® 20, 0.25%; the other impregnated with:
anilinonaphthalenesulphonic acid (ANS) 0.06%
TWEEN ® 20, 0.01%
chamber b) 2 empty fleece, 1 conjugate fleece, each of 0.5 mm thickness, impregnated with anti-T3 monoclonal antibody Fab fragment, bound to $\beta$-galactosidase 1.6 mU (Fab-E) sodium HEPES, 100 mM, pH 7.25
polyoxygelatin 1%
magnesium aspartate 5 mM
chamber c) separation matrix, 2 fleece each of 0.7 mm thickness
T3 insolubly bound to the matrix fleece
chamber AK) 1 fleece of 1 mm thickness,
chamber d) 1 fleece of 0.5 mm thickness, impregnated with
sodium HEPES, 100 mM, pH 7.25
boric acid, 5 mM
chlorophenol red galactoside 18 mM.

Liquid pipetting

5 $\mu$l of sample solution are pipetted into sample application chamber P, followed by 50 $\mu$l of diluent (physiological saline), the mixing of the components taking place by the pipetting procedure. 40 $\mu$l of diluent are pipetted into chamber c.

Carrying out of the reaction

1st Centrifuging: The liquid pipetted on to the matrix (c) is centrifuged into a reception chamber (AK). Due to this washing procedure of the matrix, hapten molecules, the binding of which to the matrix has broken during storage, are removed. These molecules would otherwise act like sample and falsify the result. The sample liquid simultaneously flows over the chamber a, thereby dissolves the reagents present therein and a pre-reaction can take place in a valve chamber VK1. The dissolving off reaction, in which the ANS dissolves the T3 from the binding with the binding proteins (preponderantly thyroxine-binding globulin (TBG)), does, not have to be complete since a further reaction in VK2 is here possible.

1st Stopping: The sample passes into chamber b, the Fab-enzyme conjugate here being dissolved off.

2nd Centrifuging: The sample is passed into VK2, the centrifuging being maintained for 5 minutes. The T3 from the sample hereby reacts with the Fab-enzyme conjugate (Fab-E) to give the complex T3.Fab-E.

2nd Stopping: The sample passes on to the fleece in chamber c. Excess Fab-E here binds to the matrix via the matrix-bound T3. This reaction lasts for 5 minutes.

3rd Centrifuging: The first part of the liquid completely fills the collection chamber AK, the greater part being centrifuged through the fleece in chamber d into VK3, the substrate hereby being dissolved from d.

3rd Stopping: The reaction solution leaves VK3.

Measurement centrifuging: The solution is transported into the cuvette K and the reaction is monitored absorption photometrically at 578 nm. The conjugate molecules which have bound T3 from the sample could pass the matrix and there is now found in the cuvette an amount of enzyme corresponding to the concentration of T3. Therefore, the measured color increase per unit time is a measure for the concentration of T3 in the sample.

Because of the proportionality between enzyme and analyte, linear calibration curves are obtained. This is shown in FIG. 2 of the accompanying drawings.

B) Determination of T3 as described hereinbefore under A, with the use of an insert element according to FIG. 1, the conjugate fleece in chamber b thereby being additionally impregnated with disulphine blue as described in Example 1.

The loading of the insert element according to FIG. 1 takes place in a manner analogous to that described under A. Only in chamber b there is used, instead of the conjugate fleece used under A, a conjugate fleece prepared according to Example 1 with disulphine blue as detectable substance.

The sequence of centrifugings and stoppings takes place as described in Section A in "carrying out of the reaction".

In addition to the absorption change measured at 578 nm, which is brought about by the enzymatic reaction, the absorption of the disulphine blue is determined at 650 nm.

C) Comparison of the results according to A) and B).

For a comparison of the results obtained according to method A) and method B), there are preferably used the variation coefficients. For this purpose, in each case n determinations of standard solutions a, b and c with known T3 concentrations (1.74 ng/ml, 2,82 ng/ml and 5.17 ng/ml, respectively) according to A) and B) are carried out. From the measurement values $X_A$ for the enzyme substrate are determined, by means of the calibration curve (FIG. 2), the related T3 concentrations $C_A$. In the case of method A), there are obtained directly herefrom the variation coefficients VK(A) according to known mathematical methods. In the case of method B), in additional to the substrate signal, there is measured a signal for the disulphine blue $X_F$. From the individual signals $X_F$, there is calculated the average value $\overline{X}_F$ of the disulphine blue valid for the test batch. Via the above-mentioned equation, for the particular measurement values $X_F$ and $C_A$ there are determined the associated corrected T3 concentrations $C_{corrected}$, in which case, as analyte-specific empirical factor f, there is used the above-given value of 0.65. The variation coefficient VK(B) can be calculated with this. The results obtained are summarized in the following:

| standard solution | T3 concentration ng./ml. | n | VK(A) % | VK(B) % |
|---|---|---|---|---|
| a | 1.74 | 32 | 6.5 | 5.1 |
| b | 2.82 | 32 | 5.6 | 4.4 |
| c | 5.17 | 32 | 4.5 | 3.4 |

The above data show that the variation coefficients for method B according to the present invention are distinctly smaller than for method A according to the prior art.

EXAMPLE 3

Determination of digoxin

A) Determination without addition of a detectable substance

Figure 3:
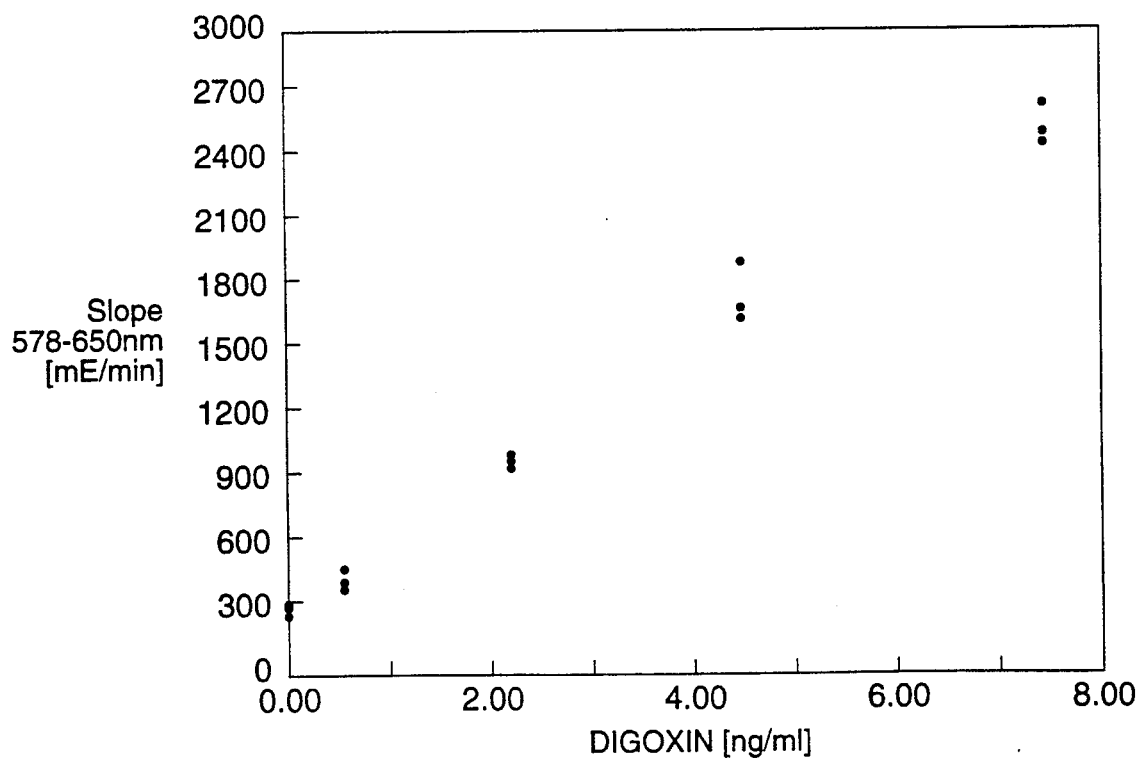
FIG. 3 is a digoxin calibration curve obtained using this invention.

The process is analogous to that of Example 2 A) but for the conjugate there are used Fab fragments of an antibody against digoxin. In this case, the matrix consists of digoxin bound to the solid phase. FIG. 3 of the accompanying drawings show the calibration curve thus obtained.

B) Determination of digoxin with addition of a detectable substance

The procedure is as described in Example 2 A) with the use of an insert element according to FIG. 1 of the accompanying drawings. The conjugate fleece in chamber b is additionally impregnated with disulphine blue as described in Example 1.

C) Comparison of the results according to A) and B)

For the comparison of the results according to method A) and method B), there are preferably used the variation coefficients.

For this purpose, in each case n determinations of standard solutions, a, b and c with known digoxin concentrations (2.03 ng/ml, 4.02 ng/ml and 6.43 ng/ml, respectively) according to A) and B) are carried out.

From the measurement values $X_A$ for the enzyme substrate are determined, by means of the calibration curve (FIG. 3), the associated digoxin concentrations $C_A$. In the case of method A), the variations coefficients VK(A) are obtained directly therefrom according to known mathematical methods. In the case of method B), in addition to the substrate signal, there is measured a signal $X_F$ for the disulphine blue. From the individual signals $X_F$, there is calculated the average value $\overline{X}_F$ of the disulphine blue valid for the test batch. Via the above-given equation, there are determined the corrected digoxin concentrations $C_{corrected}$ associated with the particular measurement values $X_F$ and $C_A$, in which case, as analyte-specific empirical factor f, there is used the above-given value of 0.5. With these can be calculated the variation coefficient VK(B). The results are summarized in the following:

| standard solution | digoxin concentration ng./ml. | n | VK(A) | VK(B) |
|---|---|---|---|---|
| a | 2.03 | 51 | 3.3 | 2.8 |
| b | 4.02 | 32 | 7.7 | 5.4 |
| c | 6.43 | 32 | 4.1 | 2.8 |

The above data show that the variation coefficients for method B according to the present invention are distinctly smaller than for method A according to the prior art.

It will be understood that the specification and examples are illustrative but not limitative of the present invention and that other embodiments within the spirit and scope of the invention will suggest themselves to those skilled in the art.

I claim:

1. Method for determining an analyte in a liquid sample, comprising:
    (i) contacting said sample to a carrier material comprising (a) a dissolvable labelled immunoreactant which specifically binds to said analyte and which reacts with said analyte to form a complex therebetween and (b) a dissolvable, detectable substance selected from the group consisting of a fluorescent dye and a colored dye which does not participate in the reaction between said analyte and said dissolvable labelled analyte specific immunoreactant and which is soluble in the same solutions and under the same conditions in which said dissolvable labelled specific immunoreactant is soluble wherein (a) and (b) dissolve from said carrier into said liquid sample to form a liquid mixture of said analyte, said labelled immunoreactant and said dissolvable detectable substance, (ii) incubating said liquid mixture with a solid phase which comprises an amount of solid phase bound analyte larger than the amount of said labelled immunoreactant, to form immune complexes between said analyte and said dissolvable labelled immunoreactant and between said solid phase bound analyte and said labelled immunoreactant (iii) separating solid phase bound immune complexes from liquid phase immune complexes;

(iv) measuring the amount of label in the liquid phase to provide a first, uncorrected value indicative of analyte concentration, (v) measuring the amount of said detectable substance in said liquid phase to determine a second measurement value which is proportional to the portion of said labelled immunoreactant dissolved from said carrier which has not formed solid phase immunecomplexes and is present in said liquid phase, and;

(vi) determining a corrected analyte concentration from the difference of said second measurement value from a mean value for said detectable substance and correcting said first uncorrected value by said difference.

2. Method of claim 1, wherein said dissolvable labelled immunoreactant is radioactively labelled, fluorometrically labelled, or enzymatically labelled.

3. Method of claim 1, wherein said dissolvable detectable substance is a patent blue dye.

4. Method for determining an analyte in a liquid sample, comprising:

(i) contacting said sample to a carrier material comprising (a) a dissolvable labelled analyte analogue and (b) a dissolvable, detectable substance selected from the group consisting of a fluorescent dye and a colored dye which is soluble in the same solutions and under the same conditions in which said dissolvable labelled analyte analogue specific immunoreactant is soluble wherein (a) and (b) dissolve in said liquid sample to form a liquid mixture of analyte, labelled analyte analogue and dissolvable detectable substance, (ii) incubating said liquid mixture with a solid phase comprising an amount of a solid phase bound immunoreactant which specifically binds to said analyte, wherein said amount is smaller than the amount of said labelled analyte analogue, to form immune complexes between said analyte and said solid phase bound immunoreactant, wherein said detectable substance dissolved in said liquid does not participate in the reaction between said solid phase bound immunoreactant and one of said analyte and said labelled analyte analogue, (iii) separating said solid phase bound immune complexes from liquid phase immune complexes, (iv) measuring the amount of label in the liquid phase to provide a first, uncorrected value indicative of analyte concentration, (v) measuring the amount of said detectable substance in said liquid phase to determine the portion of said labelled analyte analogue dissolved from said carrier, which has not formed solid phase immune complexes and is present in said liquid phase, and;

(v) determining a corrected analyte concentration from the difference of said determination of said second measurement value from a mean value for said detectable substance and correcting said first uncorrected value by said difference.

5. Method of claim 4, wherein said dissolvable labelled analyte analogue is radioactively labelled, fluorometrically labelled, or enzymatically labelled.

6. Method of claim 4, wherein said dissolvable detectable substance is a patent blue dye.

* * * * *